United States Patent [19]

Bartek et al.

[11] 4,143,082

[45] Mar. 6, 1979

[54] METHOD FOR MAKING INDENE

[75] Inventors: Joseph P. Bartek, University Heights; Robert K. Grasselli, Chagrin Falls, both of Ohio

[73] Assignee: The Standard Oil Company, Cleveland, Ohio

[21] Appl. No.: 816,638

[22] Filed: Jul. 18, 1977

[51] Int. Cl.² .......................... C07C 5/38; C07C 15/22
[52] U.S. Cl. .............................. 260/668 F; 260/668 D; 252/437
[58] Field of Search ...................... 260/668 F, 668 D; 252/437

[56] References Cited

U.S. PATENT DOCUMENTS

| | | | |
|---|---|---|---|
| 3,716,545 | 2/1973 | Ripley | 252/437 |
| 3,824,195 | 7/1974 | Pitzer | 260/668 D |
| 3,975,301 | 8/1976 | Watkins | 252/437 |
| 4,010,114 | 3/1977 | Walker et al. | 252/437 |
| 4,044,066 | 8/1977 | Ripley | 252/437 |

*Primary Examiner*—C. Davis
*Attorney, Agent, or Firm*—Herbert D. Knudsen; William D. Mooney

[57] ABSTRACT

Unsubstituted and substituted bicyclic indene precursors more saturated than indene are converted to indene by a dehydrogenation process in which the indene precursor in the presence of an oxygen donor is contacted with a phosphate catalyst.

12 Claims, No Drawings

METHOD FOR MAKING INDENE

BACKGROUND OF THE INVENTION

The present invention relates to a novel catalytic technique for making indene. More specifically, the present invention relates to a dehydrogenation process for converting indene precursors to indene by contacting the indene precursors with a phosphate catalyst at elevated temperature in the presence of an oxygen donor.

Many patents directed to copolymers containing indene as an essential component have recently issued. Unfortunately, at the present time there is no simple, straight forward and economical technique for producing indene monomer.

Accordingly, it is an object of the present invention to provide a novel technique for producing indene in a simple, economic and straight forward manner.

SUMMARY OF THE INVENTION

This and other objects are accomplished by the present invention in accordance with which an indene precursor more saturated than indene is converted into indene by an dehydrogenation reaction in which the indene precursor is contacted in the presence of an oxygen donor with a phosphate catalyst at elevated temperature. In accordance with the present invention, it has been found that a wide variety of phosphate-containing inorganic compounds will catalyze the catalytic removal of hydrogen from indene precursors more saturated than indene in the presence of an oxygen donor to thereby yield indene as a product. Thus it is possible in accordance with the present invention to produce indene by a simple and straight forward catalytic dehydrogenation reaction.

Accordingly, the present invention provides a novel dehydrogenation process for producing indene comprising contacting an indene precursor more saturated than indene and an oxygen donor with a phosphate catalyst.

DETAILED DESCRIPTION

In accordance with the present invention, indene and substituted indenes are produced from bicyclic and substituted bicyclic indene precursors more saturated than indene. The substituted bicyclic compounds may contain one or more alkyl or alkenyl groups having from 1 to 4 carbon atoms or phenyl groups attached to one or both rings. The substituted indenes produced from these precursors normally have the corresponding alkyl, alkenyl or phenyl groups attached, although they may have fewer groups, or may have groups with fewer carbon atoms attached.

Examples of precursors which may be converted into indene or substituted indenes in accordance with this invention include indane, alkyl (especially methyl) indanes in which the alkyl groups have from 1 to 4 carbon atoms, tetrahydroindene (especially the bicyclo{4.3.0-}nona-3,7-diene isomer), alkyl tetrahydroindenes in which the alkyl groups have from 1 to 4 carbon atoms, hexahydroindene, hexahydroindane and vinyl norbornene (5-vinyl bicyclo{2.2.1}- 2-heptene).

In carrying out the inventive process, the indene precursor as discussed above is contacted in the presence of an oxygen donor with a catalyst comprising a phosphate, i.e. a salt of one of the phosphoric acids. Any type of phosphoric acid salt can be employed be it an orthophosphate, a hypophosphate, a metaphosphate, a pyrophosphate, or other polyphosphates. Moreover, in the foregoing types of phosphates, any cation can be employed, and in addition different types of cations can be employed in a single phosphate. For example, an orthophosphate catalyst in accordance with the present invention can contain one, two or three different metals depending, of course, upon valence requirements, as well as hydrogen. Similarly, the other types of phosphates can contain one or more different metal cations as well as hydrogen.

Preferably, the catalysts employed in the inventive process are characterized by the following formula:

$$M_a P_x O_y$$

wherein
M is one or more elements selected from the group consisting of Mg, Sr, Ca, Ba, La, Ce, other rare earths, Cr, Mn, Fe, Co, Ni, Cu, Zn, Sn, Pb, Bi, Te, B, Al, Rh, Sb, As, U, Th, Ge and Ru;

wherein
$0.1x \leq \Sigma a \leq 10x$, wherein $\Sigma a$ represents the sum of subscripts a of all of the metal ions and y is a number such that the valence requirements of the metal ions for oxygen is satisfied.

In the foregoing catalysts, minor amounts (i.e. not more than 10% on a phosphorus atom basis) of alkali metals, noble metals, silver, gold and/or tellurium may be added.

In a more specific embodiment, the catalysts employed in the inventive process are characterized by the following formula:

$$M'_b M_a P_x O_x$$

wherein
M is at least one of Bi, Fe, Ni, Co, Cr, La, Sn, Mg, Ca, Ce, U, Sb;

wherein
M' is at least one element selected from the group consisting of Ge, Pb, Mo, W, Sr, Ba, Re, Th, As, Te, and elements selected from Groups IA, IB, IIB, IIIA and VB of the Periodic Table; and wherein
$0.1 \leq a \leq 16, 0 \leq b \leq 16, 0.5 \leq x \leq 16$ and y is a number such that the valence requirements of the remaining elements for oxygen are satisfied.

In this embodiment of the invention, particularly preferred cations are Bi, Fe, Co, Cr, La, Sn, Mg, U, Sb, Mo, W and Te when used in combinations of two or more.

Still another class of catalysts which has been found especially useful in accordance with the invention is characterized by the formula:

$$M_a X_b Bi_f P_x O_y$$

wherein
M is one or more elements selected from the group consisting of Mg, Ca, Co, Ba, Sr, Fe(II), Mn(II), Ni, Cu, Zn and Pb;

wherein
X is at least one of Fe(III), La, Cr, Ce, other rare earths, B, Al, Ru, and Rh; and wherein
$0 \leq \Sigma a + \Sigma b \leq 10x$ and $0.5 \leq X \leq 100$, wherein $\Sigma a$ + $\Sigma b$ represents the sum of all subscripts a + b and y is a number such that the valence requirements of all the other elements for oxygen is satisfied.

Specific catalysts which have been found to be useful in accordance with the present invention include $Co_{12}P_{12}O_y$, $Mg_9CrBiP_{12.5}O_y$, $Mg_9CrBiW_{0.5}P_{12.5}O_y$, $Mg_9CrBiMo_{0.5}P_{12}O_y$, $K_{0.01}Co_9LaBiP_{12}O_y$, $Co_{10}Cd_2P_{12}O_y$, $Cd_{12}P_{12}O_y$, $K_{0.1}Co_9CrBiP_{12}O_y$, $Cs_{0.02}Co_9LaBiP_{12}O_y$, $Co_{10}SbP_{12}O_y$ and $K_{0.5}Co_9LaBiP_{12}O_y$.

The catalysts employed in the inventive process can be used either as is or the catalysts can be supported on suitable inert supports such as alpha alumina, Alundum, silica, silicon carbide, titania, zirconia and the like. In addition, phosphate support materials such as $BPO_4$, $TiP_2O_7$, $ZrP_2O_7$, $SbPO_4$ and $AlPO_4$ can also be employed, wherein the catalyst support will exhibit some catalytic action of its own. The active catalytic component can be incorporated with the support by any known technique such as coprecipitation, impregnation or coating with a wet slurry, a partially dry powder or pelleting. The size of the catalyst particles is not critical and can vary between wide limits. For example, the catalyst particle size may be extremely small (e.g. microspheroidal) so that the catalyst can be employed in a fluid-bed reactor or the catalyst can be significantly larger in particle size so that the catalyst can be employed in a fixed-bed reactor.

The inventive dehydrogenation reaction is carried out in the presence of an oxygen donor. As an oxygen donor, elemental oxygen, $O_2$, is normally employed. In particular, air is normally employed as a feed since it is cheapest and most convenient. Other compounds which will serve as oxygen donors in a dehydrogenation reaction, however, can also be employed. For example, $SO_2$, COS HOCl and the like can also be employed.

The amount of oxygen donor fed to the reaction vessel should at least be the stoichiometric amount necessary to react with all of the hydrogen to be withdrawn from the indene precursor feed. Of course, less than the stoichiometric amount can be fed to the reactor, but this will simply decrease the efficiency of the process. Preferably, the amount of oxygen donor fed to the reaction vessel is at least twice, preferably 2 to 5 times, the stoichiometric amount necessary to react all of the hydrogen withdrawn from the indene precursor.

In addition to the foregoing components, a gaseous promoter known to increase oxidation rates can also be fed to the reaction vessel for improving the efficiency of the inventive dehydrogenation reaction. In this regard, it is well known that certain compounds such as halides (gaseous HCl, HBr, $Cl_2$, $Br_2$), alkyl halides of the formula $C_xH_yX_z$ wherein X is halide and x is 1–5, y is 0–16, and z is 1–16 and so forth) serve to promote various types of dehydrogenation reactions. In accordance with the present invention, such gaseous promoters can also be fed to the reaction vessel normally along with the oxygen donor (which is normally in a gaseous state) for increasing the efficiency of the inventive reaction. When a gaseous promoter is employed, it is preferable that the amount of gaseous pomoter is less than 10%, preferably less than 5%, of the oxygen donor fed to the reaction vessel in order that the hydrocarbon feed is not halogenated.

The gaseous materials fed to the reaction vessel (i.e. the oxygen donor and optionally the gaseous promoter) can also contain a gaseous diluent. Any gas inert to the reaction and catalyst can be employed as the gaseous diluent. Preferred gaseous diluents are $N_2$, $CO_2$, $H_2O$, combustion gases, light hydrocarbon gases (e.g. methane) and the like. Methane is an especially preferred gaseous diluent since it suppresses explosions and hence allows more oxygen donor to be tolerated by the system without fear of explosion. When the oxygen donor is $O_2$, the amount of inert diluent should be from 0 to 20 times the amount of $O_2$ fed to the reaction vessel. When other oxygen donors are employed, a stoichiometrically corresponding amount of inert diluent can be employed.

The inventive reaction can be carried out either in fixed-bed mode or fluid-bed mode. In fixed-bed mode, the liquid hourly space velocity of the indene precursor feed is from 0.01 to 10, preferably 0.05 to 1, optimally 0.25 hours$^{-1}$. The contact time for the reactants in the inventive process is normally from 0.1 to 20 seconds, preferably 2 to 10 seconds. The reaction pressure is normally maintained at approximately atmospheric pressure, although a lower or higher pressure can be employed if desired. Indeed, any practicable pressure can be utilized.

The reaction temperature must be at least 100° C. and is normally maintained between 100° C. and 650° C., preferably 250° C. to 550° C. In this connection, it has been found that the preferred reaction temperature varies depending upon the indene precursor to be processed with a temperature range of 350° to 600° C. being preferred for indane dehydrogenation and 200° to 550° C. being preferred for dehydrogenation of a more saturated precursor.

In order to more thoroughly illustrate the present invention, the following working examples are presented:

EXAMPLES 1 to 11

15 cc of the catalysts set forth in the following Table I were charged into a fixed-bed, $\frac{1}{2}''$ outside diameter, stainless steel, tubular reactor. Each of these catalysts was prepared by mixing an appropriate amount of each of the metals in question in the form of an aqueous nitrate solution with an aqueous solution of $NH_4H_2PO_4$ to form a precipitate, drying the precipitate and calcining the dried precipitate at a temperature of from 500° to 600° C. in air for a period of 120 to 1200 minutes. The particle size of each of the catalysts was between 20 and 35 mesh, Tyler.

In each example, a mixture of indane, approximately five parts air and three parts $N_2$ for each part indane vapor was fed to the reactor. The reactants were fed at a rate such that the liquid hourly space velocity of indane was 0.24 hr$^{-1}$ and the contact time of the reactants was about three seconds. The reaction temperature was maintained at 550° C. and the reaction pressure was one atmosphere. The following results were obtained:

TABLE I

| Example | Catalyst | Indane Converted | Indene Per Pass (Carbon Basis) | Selectivity | Indene/Indane |
|---|---|---|---|---|---|
| 1 | $Co_{12}P_{12}O_y$ | 86% | 34% | 40% | 2.4 |
| 2 | $K_{0.01}Co_9La_1Bi_1P_{12}O_y$ | 83% | 68% | 82% | 3.6 |
| 3 | $Cs_{0.02}Co_9La_1Bi_1P_{12}O_y$ | 80% | 65% | 81% | 3.3 |
| 4 | $K_{0.1}Co_9Cr_1BiP_{12}O_y$ | 81% | 66% | 82% | 3.4 |
| 5 | $Co_9LaBiP_{14}O_y$ | 66% | 50% | 76% | 1.5 |
| 6 | $Co_6Bi_4P_{12}O_y$ | 73% | 58% | 79% | 2.2 |

TABLE I-continued

| Example | Catalyst | Indane Converted | Indene Per Pass (Carbon Basis) | Selectivity | Indene Indane |
|---|---|---|---|---|---|
| 7 | $K_{0.1}Co_9CrBiP_{12}O_y$ | 80% | 63% | 80% | 3.1* |
| 8 | $Co_{4.5}Bi_4LaP_{12}O_y\{BPO_4\}_{12}$ | 61% | 47% | 77% | 1.2 |
| 9 | $K_{0.5}Co_9LaBiP_{12}O_y$ | 75% | 60% | 80% | 2.4 |
| 10 | $K_{0.5}Co_9LaBiP_{13}O_y$ | 69% | 54% | 78% | 1.7 |
| 11 | $Mg_9UBiP_{12}O_y$ | 73% | 61% | 83% | 2.3 |

*Steam rather than $N_2$ used as diluent.

As will be noted, the single pass yields realized in the foregoing experiments were in excess of 65% and selectivities in excess of 80% were obtained. It will thus be appreciated that indane was dehydrogenated to indene with very favorable per pass conversions and selectivities in a very simple manner.

EXAMPLES 12 to 17

Tetrahydroindene (bicyclo{4.3.0}nona3,7 diene) was oxydehydrogenated to indene by the same procedure and under the same conditions as in Examples 1 to 11 except that the reaction temperature was 470° C. The catalysts employed in Examples 12 to 17 were also prepared in the same way as the catalysts used in Examples 1 to 11. The results of Examples 12 to 17 are set forth in the following Table II.

TABLE II

| Example | Catalyst | THI Converted | Yields Indane | Yields Indene | Selectivity Indane & Indene | Cracking Est. |
|---|---|---|---|---|---|---|
| 12 | $Co_{12}P_{12}O_x$ | 91% (+ 9% isomerized) | 45% | 24% | 76% | 4% |
| 13 | $Co_{10}Sb_1P_{12}O_x$ | 85% | 21% | 35% | 66% | 15% |
| 14 | $K_{0.1}Co_9Cr_1BiP_{12}O_x$ | 85% | 20% | 35% | 65% | 12% |
| 15 | $K_{0.1}Co_9La_1Bi_1P_{12}O_x$ | 79% | 13% | 42% | 70% | — |
| 16 | $K_{0.5}Co_9La_1Bi_1P_{12}O_x$ | 89% (+ 11% isomerized) | 38% | 26% | 72% | 9% |
| 17 | $Cs_{0.02}Co_9La_1Bi_1P_{12}O_x$ | 78% | 13% | 38% | 65% | 12% |

As can be seen, total oxydehydrogenation selectivities in the foregoing examples were in excess of 60% and cracking of the starting material is quite small. Moreover, the recovery on a total carbon balance basis is quite high, 82–92%.

EXAMPLE 18

The procedure of Examples 12 to 17 was repeated using vinyl norbornene (5-vinyl-bicyclo{2.2.1.}-2-heptene) as the feed and a catalyst comprising $Co_7La_{1.5}Bi_2P_{12}O_x$ as a catalyst. The per pass conversion to indene was 18% while the per pass conversion to indane was 5%. Isomerization also occurred to tetrahydroindene in an amount of 14% per pass conversion. 50% of the product was cracked predominantly to butadiene and cyclopentadiene, while approximately 10% of the reactant was combusted.

EXAMPLES 19 to 40

Additional experiments were conducted in which tetrahydroindene was oxydehydrogenated to indene in the presence of air in a fixed-bed reactor. The results of these tests are summarized in the Table III.

TABLE III

| Example | Catalyst | Conversion | Yield Indane | Yield Indene | Yield THI Isomer (U.C. 200) | Selectivity Indane | Selectivity Indene | Combustion | Recovery | Reaction Temp. | C.T. | Mole Ratio THI:Air:$N_2$ |
|---|---|---|---|---|---|---|---|---|---|---|---|---|
| 19 | $K_{0.01}Co_9LaBiP_{12}O_y$ | 99 | 6 | 24 | — | 6 | 24 | 10.5 | | 530 | 3.5 | 1:5.4:2.5 |
| 20 | $K_{0.01}Co_9LaBiP_{12}O_y$ | 79.3 | 13.3 | 41.7 | — | 16.8 | 52.6 | 14.4 | 99.5 | 470 | 3.5 | 1:8:3 |
| 21 | $Co_9LaBiP_{12}O_y$, coated 20 cc | 99 | 1.3 | 7 | — | 1.3 | 7 | | | 550 | 4.5 | 1:5.4:2.3 |
| 22 | $Co_{12}P_{12}O_y$ | 100 | 45.2 | 23.7 | 8 | 45.2 | 23.7 | 8.8 | 86.8 | 470 | 3.6 | 1:5.4:2.8 |
| 23 | $Co_9LaBiP_{14}O_y$ | 78.8 | 6.8 | 21.3 | — | 8.6 | 27.0 | 9.3 | 67.8 | 470 | 3.6 | 1:5.9:2.7 |
| 24 | $Co_6Bi_4P_{12}O_y$ | 74.7 | 14.4 | 36.8 | — | 19.3 | 49.3 | 9.9 | 88.0 | 470 | 3.5 | 1:5.4:2.8 |
| 25 | $K_{0.1}Co_9CrBiP_{12}O_y$ | 85.5 | 20.5 | 34.7 | — | 24.0 | 40.6 | 11.0 | 87.7 | 470 | 3.3 | 1:5.8:3.0 |
| 26 | $Co_{4.5}Bi_4LaP_{12}O_y\cdot BPO_4{}_{12}$ | 63.7 | 9.5 | 23.8 | — | 14.9 | 37.4 | 11.1 | 87.3 | 470 | 3.4 | 1:6.1:3.0 |
| 27 | $K_{0.5}Co_9LaBiP_{12}O_y$ | 100 | 38.1 | 25.9 | 10.6 | 38.1 | 25.9 | 10.6 | 82.6 | 470 | 3.3 | 1:5.6:2.8 |
| 28 | $Co_{10}SbP_{12}O_y$ | 85.2 | 20.9 | 35.2 | — | 24.5 | 41.3 | 11.2 | 84.8 | 470 | 3.3 | 1:6.6:3.2 |
| 29 | $Co_{10}Cd_2P_{12}O_y$ | 57.2 | 5.9 | 21.3 | — | 10.3 | 37.2 | 10.6 | 85.4 | 470 | 3.5 | 1:6.2:3.1 |
| 30 | $Cd_{12}P_{12}O_y$ | 51.4 | 4.6 | 18.8 | — | 8.9 | 36.6 | 9.7 | 88.6 | 470 | 3.5 | 1:6.2:3.1 |
| 31 | $Cs_{0.02}Co_9LaBiP_{12}O_y$ | 77.9 | 12.6 | 38.1 | — | 16.2 | 48.9 | 10.5 | 91.7 | 470 | 3.1 | 1:6.0:3.0 |
| 32 | $K_{0.5}Co_9LaBiP_{13}O_y$ | 69.3 | 12.2 | 29.3 | — | 17.6 | 42.3 | 9.8 | 82.9 | 470 | 3.3 | 1:5.8:3.4 |
| 33 | $Mg_{11}Fe_{0.5}P_{12}O_y$ | 100 | 42.9 | 11.8 | 14.2 | 42.9 | 11.8 | 12.4 | 89.9 | 450 | 3.5 | 1:5.8:3.8 |
| 34 | $Cs_{0.02}Co_9LaBiP_{12}O_y$ | 75.3 | 35.4 | 23.6 | — | 47.0 | 31.3 | 7.0 | 94.6 | 425 | 3.5 | 1:5.1:3.8 |
| 35 | $Mg_9UBiP_{12}O_y$ | 100 | 44.0 | 24.0 | 5.3 | 44.0 | 24.0 | 8.8 | 85.3 | 470 | 3.4 | 1:5.2:4.0 |
| 36 | $Cs_{0.02}Co_9LaBiP_{12}O_y$ | 79.3 | 13.5 | 43.2 | — | 17.0 | 54.5 | 16.8 | 93.6 | 470 | 2.2 | 1:8.9:4.8 |
| 37 | $Mg_9UBiP_{12}O_y$ | 100 | 42.8 | 24.7 | 10.0 | 42.8 | 24.7 | 19.1 | 88.9 | 425 | 3.5 | 1:9.6:0 |
| 38 | $Mg_9CrBiP_{12.5}O_y$ | 98.1 | 32.9 | 49.3 | — | 33.5 | 50.2 | 5.5 | 102.9 | 470 | 3.5 | 1:5.6:3.3 |
| 39 | $Mg_9CrBiMo_{0.5}P_{12}O_y$ | 100 | 33.0 | 46.3 | — | 33.0 | 46.3 | 11.1 | 79.3 | 470 | 3.4 | 1:6.0:3.0 |
| 40 | $Mg_9CrBiW_{0.5}P_{12}O_y$ | 99.2 | 34.4 | 38.4 | — | 34.7 | 38.7 | 10.1 | 87.4 | 470 | 3.2 | 1:5.9:2.9 |

As will be noted, indene is produced with high yields in substantially all of the foregoing examples.

Although only a few embodiments of the present invention have been described above, it should be appreciated that many modifications can be made without departing from the spirit and scope of the present invention. For example, it should be apprecated that in addition to the various indene precursors described above as starting materials substituted indene precursors, especially alkyl substituted indene precursors of the foregoing type in which the alkyl groups have from 1 to 4 carbon atoms can also be employed. Furthermore, the hydrocarbon starting material can comprise a mixture of different indene precursors as well as a single indene precursor. In this regard, it is contemplated that the reaction product obtained by carrying out a Diels-Alder reaction on cyclopentadiene and butadiene, which normally contains both tetrahydroindene and vinyl norbornene, can be directly processed in accordance with the present invention to form indene. It should also be appreciated that it is possible and may be preferable in accordance with the present invention to recycle indene precursor byproduct of the inventive process in order to further treat these indene precursors to form indene therefrom. In addition, since cyclopentadiene and butadiene are the predominant cracking products of the inventive reaction, it is also possible to subject these byproducts to a Diels-Alder reaction to form tetrahydroindene and vinyl norbornene which in turn can be used as a starting material in the inventive process.

Finally, it should be appreciated that the phosphate catalysts employed in the inventive process can be prepared in any conventional manner, such as by using a nitrate solution as discussed above or any other convenient technique.

Although only a few embodiments of the present invention have been described above, many modifications can be made without departing from the spirit and scope of the invention. All such modifications are intended to be included within the scope of the present invention which is to be limited only by the following claims:

We claim:

1. A dehydrogenation process for producing unsubstituted or substituted indene from an unsubstituted or substituted bicyclic indene precursor more saturated than indene, said substituted indene precursor being substituted with at least one of $C_1$-$C_4$ alkyl, $C_1$-$C_4$ alkenyl and phenyl, said process comprising contacting said indene precursor and an oxygen donor with a phosphate catalyst represented by the formula:

$$M_aP_xO_y$$

wherein
M is one or more elements selected from the group consisting of Mg, Sr, Ca, Ba, La, Ce, other rare earths, Cr, Mn, Co, Ni, Cu, Zn, Pb, Bi, Te, B, Al, Rh, Sb, As, Ge, U, Th and Ru; and
wherein
$0.1 \times \leq a \leq 10x$, wherein a represents the sum of subscript a of all of the metal ions and y is a number such that the valence requirements of the metal ions for oxygen is satisfied.

2. The process of claim 1 wherein the reaction temperature of said process is at least 100° C.

3. The process of claim 2 wherein said indene precursor is selected from the group consisting of indane, alkyl indanes in which the alkyl groups have from 1 to 4 carbon atoms, tetrahydroindene, alkyl tetrahydroindenes in which the alkyl groups have from 1 to 4 carbon atoms, hexahydroindene, hexahydroindane and vinyl norbornene.

4. The process of claim 1 wherein said oxygen donor is $O_2$.

5. The process of claim 4 wherein said reaction temperature is 100° to 650° C.

6. The process of claim 5 wherein said reaction temperature is 250° to 550° C.

7. The process of claim 1 wherein said phosphate catalyst consists essentially of a composition represented by the formula:

$$M_aP_xO_y$$

wherein
M is one or more elements selected from the group consisting of Mg, Sr, Ca, Ba, La, Ce, other rare earths, Cr, Mn, Co, Ni, Cu, Zn, Pb, Bi, Te, B, Al, Rh, Sb, As, Ge, U, Th and Ru; and
wherein
$0.1 \times \leq a \leq 10x$; wherein a represents the sum of subscripts a of all of the metal ions and y is a number such that the valence requirements of the metal ions for oxygen is satisfied.

8. The process of claim 3 wherein said phosphate catalyst consists essentially of a composition characterized by the formula:

$$M'_bM_aP_xO_y$$

wherein
M is at least one of Bi, Ni, Co, Cr, La, Mg, Ca, Ce, U, Sb;
wherein
M' is at least one element selected from the group consisting of Ge, Pb, Mo. W, Sr, Be, Re, Th, As, Te, and elements selected from Groups IB, IIB, IA, IIIA, and VB of the Periodic Table; and
wherein
$0.1 \leq a \leq 16$, $0 \leq b \leq 16$, $0.5 \leq x \leq 16$ and y is a number such that the valence requirements of the remaining elements for oxygen are satisfied.

9. The process of claim 8 wherein said phosphate catalyst contains at least one of Bi, Sn, Co, Cr, La, Sn, Mg, U and Sb, and further wherein said catalyst contains at least one of Mo, W and Ti.

10. The process of claim 3 wherein said catalyst is selected from the group consisting of $Co_{12}P_{12}O_y$, $Mg_9CrBiP_{12.5}O_y$, $Mg_9CrBiW_{0.5}P_{12.5}O_y$, $Mg_9CrBiMo_{0.5}P_{12}O_y$, $K_{0.01}Co_9LaBiP_{12}O_y$, $Co_{10}Cd_2P_{12}O_y$, $Cd_{12}P_{12}O_y$, $K_{0.1}Co_9CrBiP_{12}O_y$, $Cs_{0.02}Co_9LaBiP_{12}O_y$, $Co_{10}SbP_{12}O_y$ and $K_{0.5}Co_9LaBiP_{12}O_y$.

11. The process of claim 3 wherein said indene precursor is so selected that indene is produced by said process.

12. The process of claim 3 wherein said phosphate catalyst consists essentially of a composition characterized by the formula:

$$M_aX_bBi_fP_xO_y$$

wherein
M is one or more elements selected from the group consisting of Mg, Ca, Co, Ba, Sr, Mn (II), Ni, Cu, Zn and Pb;
wherein
X is at least one of La, Cr, Ce, other rare earths, B, Al, Ru and Rh; and
wherein
$0 \leq a + b \leq 10x$ and $0.5 \leq x \leq 100$, and wherein a + b represents the sum of all subscripts a and all subscripts b and y is a number such that the valence requirements of the other elements for oxygen is satisfied.

* * * * *